(12) United States Patent
Lu et al.

(10) Patent No.: US 10,314,847 B2
(45) Date of Patent: Jun. 11, 2019

(54) SCALARANE SESTERTERPENOID, PHARMACEUTICAL COMPOSITION AND TOPOISOMERASE II AND HSP90 INHIBITOR FOR TREATING CANCER, AND USE AND PREPARATION METHOD THEREOF

(71) Applicant: NATIONAL DONG HWA UNIVERSITY, Hualien (TW)

(72) Inventors: Mei-Chin Lu, Pingtung County (TW); Ping-Jyun Sung, Hualien (TW); Jui-Hsin Su, Hualien (TW); Kuei-Hung Lai, Hualien (TW); Yi-Chang Liu, Hualien (TW); Ying-Chi Du, Chiayi (TW); Yu-Ming Hsu, Kaohsiung (TW); Ming-Kai Weng, Hualien (TW); Fu-Wen Kuo, Hualien (TW)

(73) Assignee: National Dong Hwa University, Hualien (TW)

( * ) Notice: Subject to any disclaimer, the term of this patent is extended or adjusted under 35 U.S.C. 154(b) by 0 days.

(21) Appl. No.: 15/676,102

(22) Filed: Aug. 14, 2017

(65) Prior Publication Data

US 2018/0271879 A1    Sep. 27, 2018

(30) Foreign Application Priority Data

Mar. 23, 2017    (TW) .............................. 106109821 A (51) Int. Cl.
  *A61K 31/56*    (2006.01)
  *A61K 35/655*   (2015.01)
  *A61K 31/122*   (2006.01)

(52) U.S. Cl.
  CPC ............ *A61K 31/56* (2013.01); *A61K 31/122* (2013.01); *A61K 35/655* (2015.01)

(58) Field of Classification Search
  CPC .................................................... A61K 31/56

(Continued)

(56) References Cited

FOREIGN PATENT DOCUMENTS

| CN | 101888777 A | 11/2010 |
|----|-------------|---------|
| CN | 106470696 A | 3/2017 |

OTHER PUBLICATIONS

Gura et. al. (Science, 1997, 278:1041-1042) (Year: 1997).*

(Continued)

*Primary Examiner* — Dennis Heyer
*Assistant Examiner* — Rayna Rodriguez
(74) *Attorney, Agent, or Firm* — Volpe and Koenig, P.C.

(57) ABSTRACT

The present invention discloses scalarane sesterterpenoids represented by formula (I) and meroditerpenoid represented by formula (II), which are extracted from *Carteriospongia* sp. sponge:

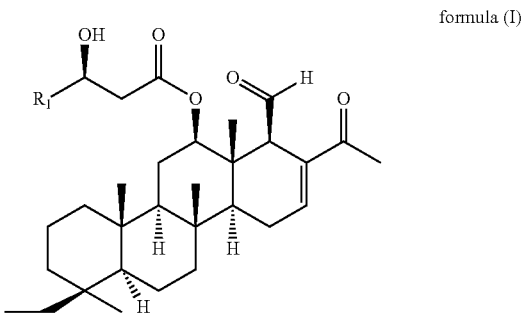

formula (I)

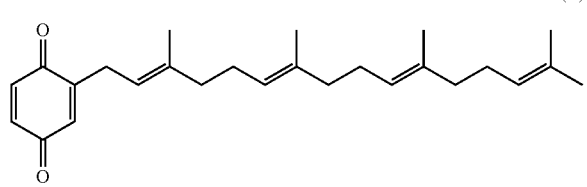

formula (II)

where $R_1$ is $-CH_3$ or $-C_2H_5$. The compounds of formula (I) can be used to be an anticancer, act as an inhibitor targeting to topoisomerase II and hsp90 and a pharmaceutical composition for anticancer.

5 Claims, 11 Drawing Sheets

(58) Field of Classification Search
USPC .......................................................... 514/510
See application file for complete search history.

(56) References Cited

OTHER PUBLICATIONS

Johnson et. al. (British Journal of Cancer, 2001, 84:1424-1431) (Year: 2001).*
Lai et al (Scientific Reports, 2016; 6:36170, p. 1-14) (Year: 2016).*
Bowden et al (J Nat Prod, 1992; 55(9):1234-1240) (Year: 1992).*
Morris et al., "AutoDock4 and AutoDockTools4: Automated Docking with Selective Receptor Flexibility," J. Comput Chem. Dec. 2009; 30(16): 2785-2791.
The 31st Symposium on Natural Products & Symposium on Pharmacy and Traditional Chinese Medicine, Oct. 14-15, 2016, 63 pages.
Lai et al., "Antileukemic Scalarane Sesterterpenoids and Meroditerpenoid from *Carteriospongis* (*Phyllospongia*) sp., Induce Apoptosis via Dual Inhibitory Effects on Topoisomerase II and Hsp90," Scientific Reports, published Oct. 31, 2016; 6:36170 14 pages.
National Dong Hwa University, "Chemical Constituests and Biological Activities of the Formosan Sponge *Carteriospongia* (*Phyllospongia*) sp.", 105 pgs. (English Abstract, p. VIII).

\* cited by examiner

SCALARANE SESTERTERPENOID, PHARMACEUTICAL COMPOSITION AND TOPOISOMERASE II AND HSP90 INHIBITOR FOR TREATING CANCER, AND USE AND PREPARATION METHOD THEREOF

CROSS REFERENCE TO RELATED APPLICATION

This application claims the benefit of Taiwan Patent Application No. 106109821, which was filed Mar. 23, 2017 at the Taiwan Intellectual Property Office and is incorporated herein by reference as if fully set forth.

FIELD OF THE INVENTION

The present invention is related to a sesterterpenoid and a pharmaceutical composition. In particular, the present invention is related to a scalarane sesterterpenoid, a pharmaceutical composition and a topoisomerase II inhibitor for treating cancer, and the use and preparation method thereof.

BACKGROUND OF THE INVENTION

Cancer refers to an organism's abnormal cellular proliferation, and these abnormally proliferated cells may invade other parts of the organism. There are many factors that cause cancer, such as obesity, poor nutrition, insufficient exercise, alcohol, infection, radiation, environmental pollution factors, genetics, viral infections and so on.

Because of the fast pace of today's society, pollution, and more sedentary lifestyles, cancer has become a major cause of death in many countries, especially in developed countries. People of every age and stage may suffer from cancer during their lives. Because DNA damage is one of the reasons that causes cancer, and because that may increase as people age, the risk of cancer is also increasing.

Cancer may be treated with surgery, chemotherapy, radiotherapy, immunotherapy, monoclonal antibody therapy and so on. The treatment method depends on the position of any tumor, malignancy, progress, patient's condition and so on.

Heat shock proteins (Hsp) include a certain group of highly conserved stress proteins which have attracted attention due to their overexpression in cancer tissues. Overexpression of these Hsp proteins is related to metastatic potential, resistance to chemotherapy and poor prognosis. Hsp proteins are named depending on their molecular weight (such as Hsp60, Hsp70 and Hsp90) and among the most studied protein is Hsp90. This protein is the most prominent member of the highly abundant chaperone proteins and it is essential for folding nascent polypeptide to control the activity, stability and protein sorting. Hsp90 has been identified as a promising drug target for cancer treatment, because it can stabilize and activate a variety of survival proteins to maintain cancer phenotype and help cancer cells to overcome multiple environmental stresses. There is considerable interest in developing potential Hsp90 inhibitors with a much simpler rationale through the depletion of oncogenic Hsp90 clients. Tanespimycin (17-allylamine-17-demethoxygeldanamycin, 17-AAG), the first Hsp90 inhibitor, was found to bind to the N-terminal regulatory pocket of Hsp90 and thus inhibiting its function. However, further clinical development of 17-AAG was halted because of poor solubility, limited bioavailability, and unacceptable hepatotoxicity.

Another important group of proteins, topoisomerases (Topo), have also attracted attention due to their crucial role in cell survival and replication. Topoisomerases are classified into two main classes: topoisomerase I (Topo I) and topoisomerase II (Topo II), wherein Topoisomerase II is composed of two isoforms, α and β, which share highly similar amino acid sequence (up to 70%). Topo IIα is essential for the survival of proliferating cells and can distinguish the handedness of DNA supercoils during relaxation reactions. However, Topo IIβ is dispensable at the cellular level. Topo II disentangle topological problems, which regulate DNA replication, transcription and chromosome segregation, and processes related to tumorigenesis. Inhibition of Topo II activity is one of the current therapeutic protocols targeting several cancers including lung, breast, lymphomas, testicular and sarcomas. The inhibition of Topo II activity is achieved either with poisons, which interfere with the topoisomerase-DNA complex or inhibitors, which suppress the catalytic turnover. Despite the effectiveness of Topo II poisons as anticancer drugs, they can trigger chromosomal breaks leading to secondary leukemogenesis.

Although there are techniques and research for treating cancer described above or not described herein, scientists still endeavor to find novel and efficient techniques, drugs and therapies for cancer treatments.

It is therefore the Applicant's attempt to deal with the above limitations in the prior art.

SUMMARY OF THE INVENTION

To develop novel topoisomerase II (Topo II) inhibitors and prepare the Topo II inhibitors as pharmaceutical compositions for treating cancer, novel scalarane sesterterpenoids (represented as the following compound of formula (I)) are isolated and purified from the sponge animal, *Carteriospongia* sp. in the present invention:

formula (I)

where $R_1$ is one of —$CH_3$ and —$C_2H_5$. The compound of formula (I) is 12β-(3'β-hydroxybutanoyloxy)-20,24-dimethyl-24-oxo-scalara-16-en-25-al when $R_1$ is —CH3, and the compound of formula (I) is 12β-(3'β-hydroxypentanoyloxy)-20,24-dimethyl-24-oxo-scalara-16-en-25-al when $R_1$ is —$C_2H_5$.

In addition, a compound of formula (II) which is nominated as 2-tetraprenil-1,4-benzochinone is also isolated and purified from *Carteriospongia* sp. in the present invention.

formula (II)

Therefore, the present invention discloses a topoisomerase II inhibitor, including the compound of formula (I) above. In one embodiment, the topoisomerase II inhibitor further includes the compound of formula (II) above.

In one embodiment, the topoisomerase II inhibitor inhibits an activity of a topoisomerase II in a cancer cell, which is correlated to a cancer included but not limited to leukemia, lymphoma, oral cancer, prostate cancer, colon cancer, breast cancer and the like. In one embodiment, the cancer cell correlated to the leukemia includes, but is not limited to, human chronic myelogenous leukemia cell line K562 (ATCC® CCL-243™), human acute lymphoblastic leukemia cell line Molt 4 (ATCC® CRL-1582™), human acute promyelocytic leukemia cell line HL60 (ATCC® CCL-240™ and the like. In one embodiment, the cancer cell correlated to the lymphoma includes, but is not limited to, human histiocytic lymphoma cell line U937 (ATCC® CRL-1593.2™), human T-cell lymphoblastic lymphoma cell line Sup-T1 (ATCC® CRL-1942™) and the like. In one embodiment, the cancer cell correlated to the oral cancer includes, but is not limited to, human gingival squamous cell carcinoma cell line Ca9-22 (Japanese Collection of Research Biosources Cell Bank, JCRB0625), human squamous cell carcinoma cell line Cal-27 (ATCC® CRL-2095™ and the like. In one embodiment, the cancer cell correlated to the prostate cancer includes, but is not limited to, human prostate adenocarcinoma cell line LNCaP (ATCC® CRL-1740™). In one embodiment, the cancer cell correlated to the colon cancer includes, but is not limited to, human colorectal adenocarcinoma cell line DLD-1 (ATCC® CCL-221™) and the like. In one embodiment, the cancer cell correlated to the breast cancer includes, but is not limited to, human ductal carcinoma cell line T-47D (ATCC® HTB-133™) and the like.

The present invention further discloses a treatment method for treating a cancer with a pharmaceutical composition prepared by a pharmaceutically effective amount of a topoisomerase II inhibitor of formula (I) above.

The present invention further discloses a preparation method of the topoisomerase II inhibitor of formula (I), including steps of: (a) providing a sponge animal; (b) extracting the sponge animal with ethyl acetate to obtain an ethyl acetate extract; (c) concentrating the ethyl acetate extract to obtain a residue; and (d) chromatographing the residue to obtain the topoisomerase II inhibitor of formula (I). In one embodiment, the sponge animal includes but is not limited to Carteriospongia sp.

In one embodiment, the step (a) further includes: (a1) freeze-drying the sponge animal; and (a1) mincing the sponge animal. In one embodiment, the step (c) is performed by evaporation under reduced pressure. In one embodiment, the step (d) further includes: (d1) sequentially chromatographing the residue with n-hexane, a plurality of n-hexane-EA mixtures of an increasing polarity, and acetone on the silica gel to obtain a plurality of fractions; and (d2) purifying at least one of the plurality of fractions with the normal phase high performance liquid chromatography (HPLC) to obtain the topoisomerase II inhibitor of formula (I). In one embodiment, the step (d) further includes: (d1) sequentially chromatographing the residue with n-hexane, a plurality of n-hexane-EA mixtures of an increasing polarity, and acetone on the silica gel to obtain a plurality of fractions; and (d2) purifying at least one of the plurality of fractions with the normal phase HPLC to obtain the topoisomerase II inhibitor of formula (II).

The present invention discloses a topoisomerase II inhibitor including the compound of formula (I) above, which thus inhibits the topo II activity of cancer cells and can be used as an anticancer pharmaceutical composition.

The present invention discloses a method for treating a cancer of a subject, including: administering a pharmaceutically effective amount of a topoisomerase II inhibitor of formula (I) to the subject in need thereof.

The term "90% methanol solution" described herein refers to a solution being mixed by methanol ($CH_3OH$) and $H_2O$ at a volume ratio of 9:1. The term "methanol solution" described herein refers to a solution being mixed by $CH_3OH$ and $H_2O$ at a specific volume ratio, which is not limited to 9:1. The skilled person in the art can understand that a methanol solution at other $CH_3OH/H_2O$ volume ratio may be applied in the invention and fails within the protection scope of claims.

The term "n-hexane-ethyl acetate mixture" described herein is a mixture being prepared by n-hexane and ethyl acetate at the various volume ratio. Other mixtures and solutions described herein, if not particularly indicated, means that they are prepared by the components and water/solvent at a specific volume ratio.

BRIEF DESCRIPTION OF THE DRAWINGS

The objectives and advantages of the present invention will become more readily apparent to those ordinarily skilled in the art after reviewing the following detailed descriptions and accompanying drawings.

DETAILED DESCRIPTION OF THE PREFERRED EMBODIMENTS

The present invention will now be described more specifically with reference to the following embodiments. It is to be noted that the following descriptions of preferred embodiments of this invention are presented herein for purpose of illustration and description only; they are not intended to be exhaustive or to be limited to the precise form disclosed.

Extraction and Isolation:

The specimen of Carteriospongia sp. was collected by scuba diving at a depth of 14 m from coral reefs off the coast of Tai-tung, Taiwan in March, 2013. Voucher specimen was deposited in the National Museum of Marine Biology and Aquarium, Taiwan (specimen No. 2013-03-SP-3). Taxonomic identification was performed by the National Sun Yat-sen University, Kaohsiung, Taiwan. Because Carteriospongia sp. can be easily obtained and identified by the skilled person in the art, there is no need to reserve this biological material according to the Patent Law and its Implementing Regulations.

Carteriospongia sp. (440 g fresh weight) was collected and freeze-dried. The freeze-dried material was minced and extracted exhaustively with ethyl acetate (EtOAc, 6×2 L). The EtOAc extract was evaporated under reduced pressure to afford a residue (5 g), and the residue was subjected to column chromatography on silica gel, using n-hexane, n-hexane and EtOAc mixture of increasing polarity, and finally pure acetone to yield 8 fractions: Fr-1 (eluted by n-hexane:EtOAc, 50:1 (v/v)), Fr-2 (eluted by n-hexane:EtOAc, 25:1 (v/v)), Fr-3 (eluted by n-hexane:EtOAc, 10:1 (v/v)), Fr-4 (eluted by n-hexane:EtOAc, 5:1 (v/v)), Fr-5 (eluted by n-hexane:EtOAc, 2:1 (v/v)), Fr-6 (eluted by n-hexane:EtOAc, 1:1 (v/v)), Fr-7 (eluted by EtOAc) and Fr-8 (eluted by acetone). Fraction 2 (560.0 mg) was separated by normal phase HPLC with gradient elution (n-hexane:EtOAc=50:1 (v/v) to 25:1 (v/v)) to yield 15 subfractions (2A-2O). Subfraction 21 was separated by normal phase HPLC (n-hexane:EtOAc=40:1 (v/v)) to afford compound 3 (70.0 mg). Fraction 5 (320.0 mg) was further purified with silica gel (n-hexane:EtOAc=4:1 (v/v) to 1:1 (v/v)) to afford 10 subfractions (5A-5J). Subfraction 5E was then separated by normal phase HPLC (n-hexane:EtOAc=3:1 (v/v)) to obtain compound 2 (6.0 mg). Subfraction 5G was separated by normal phase HPLC (n-hexane:EtOAc=3:1 (v/v)) to afford compound 1 (4.1 mg).

Compound 1:

12β-(3'β-hydroxybutanoyloxy)-20,24-dimethyl-24-oxoscalara-16-en-25-al: colorless oil; $[\alpha]_D^{25}$+10.7 (c 0.41, CHCl$_3$); IR (neat) $v_{max}$ 3448, 2963, 2931, 2875, 1718, 1666, 1374 and 1272 cm$^{-1}$; $^{13}$C and $^1$H NMR data, see Table 1; ESIMS m/z 523[M+Na]$^+$; HRESIMS m/z 523.3397 [M+Na]$^+$ (calcd for C$_{31}$H$_{48}$O$_5$Na, 523.3399).

Compound 2:

12β-(3'β-hydroxypentanoyloxy)-20,24-dimethyl-24-oxoscalara-16-en-25-al (2): colorless oil; $[\alpha]_D^{25}$+5.7 (c 0.50, CHCl$_3$); IR (neat) $v_{max}$ 3448, 2930, 2854, 1730, 1666, 1388 and 1281 cm$^{-1}$; $^{13}$C and $^1$H NMR data, see Table 1; ESIMS m/z 537[M+Na]$^+$; HRESIMS m/z 537.3546 [M+Na]$^+$ (calcd for C$_{32}$H$_{50}$O$_5$Na, 537.3550).

Preparation of (R)- and (S)-MTPA Esters (2r and 2s):

A small amount of compound 2 (2.5 mg) was divided, stored in two nuclear magnetic resonance (NMR) tubes and dried under vacuum. Deuterated pyridine (0.60 mL) and (R)-MTPA-Cl (12 μL) were added to one of the NMR tubes. The reaction NMR tubes were permitted to stand at room temperature and monitored by 400 MHz NMR every hour. After 3 hours, the reaction was found to be completed, and the $^1$H NMR data was obtained (400 MHz, in C$_5$D$_5$N). The (S)-MTPA ester of compound 2 (compound 2s) was obtained, and the $^1$H NMR data was analyzed. Similar to compound 2s, (S)-MTPA-Cl (12 μL) and deuterated pyridine (0.60 mL) were reacted at room temperature for 3 hours, to afford the (R)-MTPA ester derivative (compound 2r), in separate experiment, and the $^1$H NMR spectrum was measured with 400 MHz NMR in C$_5$D$_5$N. (S)-MTPA ester (compound 2s): $^1$H NMR (400 MHz, C$_5$D$_5$N): δ9.928 (d, J=3.6 Hz, 1H, H-25), 7.015 (s, 1H, H-16), 5.810 (t, J=6.4 Hz, 1H, H-3'), 5.027 (dd, J=10.8, 4.8 Hz, 1H, H-12), 3.253 (s, 1H, H-18), 2.255 (s, 3H, H-26), 1.134 (s, 3H, H-23), 1.110 (t, J=6.0 Hz, 3H, H-5'), 0.882 (s, 3H, H-21), 0.793 (s, 3H, H-22), 0.776 (s, 3H, H-19), 0.743 (t, J=7.2 Hz, 3H, H-25). (R)-MTPA ester (compound 2r): $^1$H NMR (400 MHz, C$_5$D$_5$N): δ 10.018 (d, J=4.0 Hz, 1H, H-25), 7.065 (s, 1H, H-16), 5.833 (t, J=6.4 Hz, 1H, H-3'), 5.123 (dd, J=11.2, 4.0 Hz, 1H, H-12), 3.393 (s, 1H, H-18), 2.259 (s, 3H, H-26), 1.142 (s, 3H, H-23), 1.060 (t, J=6.4 Hz, 3H, H-5'), 0.885 (s, 3H, H-21), 0.797 (s, 3H, H-22), 0.780 (s, 3H, H-19), 0.745 (t, J=7.2 Hz, 3H, H-25).

Bioassay Materials:

The cell lines were obtained from the American Type Culture Collection (ATCC, Manassas, Va., U.S.A.) or the Japanese Collection of Research Biosources (JCRB) Cell Bank (Japan). Cells were maintained in RPMI 1640 medium supplemented with 10% fetal calf serum, 2 mM glutamine and antibiotics (100 units/mL of penicillin and 100 μg/mL of streptomycin) at 37° C. in a humidified atmosphere of 5% CO$_2$. Antibodies against c-PARP, caspases 8, 9, 7 and 3, γH2AX, Bip, Grp 94, p-GSK 313 (Ser$^9$), p-c-Raf, p70$^{S6K}$, Hsp 90, Hsp 70, Rb 2, MDM2, HIF 1, PERK and IRE 1 were purchased from Cell Signaling Technologies (Beverly, Mass., U.S.A.). Antibodies against XIAP, NFκB (p65), GADD, CDK 4, HSF 1, ATF 6 and β-tubulin were obtained from Santa Cruz Biotechnology (Santa Cruz, Calif., U.S.A.). The Hybond ECL transfer membrane and ECL Western blotting detection kits were obtained from Amersham Life Sciences (Amersham, U.K.).

Annexin V/Propidium Iodide (PI) Apoptosis Assay:

The externalization of phosphatidylserine (PS) and membrane integrity were quantified using an annexin V-fluorescein isothiocyanate (annexin V-FITC) staining kit. In brief, 10$^6$ cells were grown in 35 mm diameter plates and were labeled with annexin V-FITC (10 μg/mL) and PI (20 μg/mL) prior to harvesting. After labeling, all plates were washed with a binding buffer and harvested. Cells were resuspended in the binding buffer at a concentration of 2×10$^5$ cells/mL before analysis by flow cytometer FACS-Calibur (Becton-Dickinson, San Jose, Calif., U.S.A.) and CellQuest software. Approximately 10,000 cells were counted for each determination.

Determination of Reactive Oxygen Species (ROS) Generation, Calcium Accumulation, and Matrix Metalloproteinase (MMP) Disruption:

MMP disruption, calcium accumulation and ROS generation were detected with the JC-1 cationic dye (5 µg/mL), the fluorescent calcium indicator (Fluo 3, 5 mM) and the carboxy derivative of fluorescein (carboxy-H2DCFDA, 1.0 mM), respectively. In brief, the treated cells were labeled with a specific fluorescent dye for 30 minutes. After labeling, cells were washed with PBS and resuspended in PBS at a concentration of $1 \times 10^6$ cells/mL before analysis via flow cytometry.

Assay of Topoisomerase II Catalytic Inhibitors and Poisons:

The assay was performed as described in the literatures (Shih et al., Marine Drugs, 2014, 12(5):3072-3090 and Shih et al., Marine drugs, 2015, 13(5):3132-3153). Standard relaxation reaction mixtures (20 µL) containing 50 mM Tris-HCl (pH 8.0), 10 mM $MgCl_2$, 200 mM potassium glutamate, 10 mM dithiothreitol, 50 µg/mL bovine serum albumin (BSA), 1 mM ATP, 0.3 µg of pHOT1 plasmid DNA, 2 units of human topoisomerase II (Topogen, Columbus, Ohio, U.S.A.), and the indicated concentrations of etoposide and the compounds 1 to 3 were incubated at 37° C. for 30 minutes. Reactions were terminated by adding 2 µL of 10% SDS to facilitate trapping the enzyme in a cleavage complex, followed by the addition of 2.5 µL of proteinase K (50 µg/mL) to digest the bound protein (incubated at 37° C. for 15 minutes) and finally by adding 0.1 volume of the sample loading dye. The DNA products were analyzed via electrophoresis through vertical 2% agarose gels at 2 voltage/cm in 0.5×TAE buffer. Gels were stained with ethidium bromide (EtBr) and photographed using an Eagle Eye II system (Stratagene, La Jolla, Calif., U.S.A.). The quantitative analysis of the DNA Topo II activity was performed. The gels were directly scanned with an image analyzer, and the area representing supercoiled DNA calculated to evaluate the concentration that the compounds caused 50% inhibition ($IC_{50}$) of Topo II activity.

Neutral Comet Assay for Detection of DNA Double-Strand Breaks (DSBs):

The assay was carried out using a CometAssay™ Kit (Trevigen, Gaithersburg, Md., U.S.A.) following the manufacturer's protocol for the neutral Comet assay. Briefly, cancer cells ($2 \times 10^5$ cells/mL) were treated with compound 1 (0.0625 µg/mL) at the indicated time. Cells were combined with 1% low melting point agarose at a ratio of 1:10 (v/v) and immediately 75 µL of the mixture was pipetted onto CometSlide™ and allowed to set at 4° C. in the dark. The slides were immersed in an ice-cold lysis solution (Trevigen) for 30 to 60 minutes. The slides were placed in a horizontal electrophoresis apparatus and electrophoresed in 1×TBE (90 mM Tris-HCl, 90 mM boric acid, and 2 mM EDTA, pH 8.0) at 20 V for 10 minutes. The samples were then fixed in 70% ethanol and dried before stained with 1:10,000 SYBR Green I (Trevigen) to visualize cellular DNA. The fluorescence images were analyzed using the TriTek Comet Image program to circumscribe the "head" and the "tail" regions of each comet and the integrated fluorescence values of each defined area were recorded. The comet length was measured from the trailing edge of the nucleus to the leading edge of the tail. This length was indicative of the extent of DNA damage. Calculations were averaged per replicate. The results were expressed as mean±standard deviation (SD) (*p<0.05).

Immunofluorescence Analysis:

After treatment with the tested compound, cells were fixed with 4% paraformaldehyde in 50 mM HEPES buffer (pH 7.3) for 30 minutes, and permeabilized for 20 minutes with 0.2% Triton X-100 in PBS (pH 7.4). To prevent non-specific protein binding, cells were incubated with 5% BSA in PBS containing 0.05% Trition X-100 (T-PBS) for 1 hour at room temperature. Cells were then incubated with the primary Hsp70 antibodies (1:500) for 2 hours and further with secondary antibodies (Alexa Fluor 586-conjugated goat anti-mouse IgG (H+L) (Life Technologies, Carlsbad, Calif., U.S.A.)) diluted at 1:1000 for 1 hour at room temperature. After washing with PBS, cells were observed under a FV1000 confocal laser scanning microscope (Olympus, Tokyo, Japan).

Human Leukemia Molt 4 Cells Xenograft Animal Model:

Six-week-old male immunodeficient athymic mice were purchased from the National Laboratory Animal and Research Center (Taipei, Taiwan). All of the animals were maintained under standard laboratory conditions (temperature 24-26° C., 12-12 hour dark-light circle) and fed with a laboratory diet and water. Molt 4 cells ($1 \times 10^6$) resuspended in 0.2 mL PBS were injected subcutaneously (s.c.) into the right flank of each mouse, and tumor growth was monitored every day. Fourteen (14) days after tumor cell injection, mice with confirmed tumor growth were randomly divided into two groups. Compound 3 (1.14 µg/g) was intraperitoneally administered to the treatment group, and the control group received solvent only. Compound 3 was administrated every other day for 33 days. Animals were sacrificed by carbon dioxide. Tumor size was measured three times a week using calipers and tumor volumes were calculated according to the standard formula: $width^2 \times length/2$.

Molecular Modeling Assay:

The molecular docking was performed by Autodock 4.2 with Lamarckian Genetic Algorithm (Morris et al., J. Comput. Chem., 2009, 30(16):2785-2791.). The target macromolecule, Hsp90 protein (PDB ID: 1YET), was obtained from the Protein data bank (http://www.rcsb.org/pdb/home/home.do). The co-crystalized protein substrates, including ligands, water and small molecules were removed, and the Polar hydrogens and Kallman united atom charges were added to the protein for docking calculation by AutoDock Tool 1.5.4 interfaces (ADT). The ligands were optimized with MMFF94 force field by ChemBio3D software (version 11.0; Cambridge Soft Corp.). Polar hydrogens and Gasteiger charges were also added to the ligand for docking study by ADT. The Grid box calculated by AutoGrid program was centered at the activity site of Hsp90 with dimensions 56×56×56 Å grid points at spacing of 0.375 Å and its size is big enough to allow the ligand move freely in the search space. All docking parameters were set to default except for the following parameter: maximum number of energy evaluation increase to 25,000,000 per run. The docking results were analyzed by ADT and shown by Accelrys Discovery Studio v3.5 client software (Accelrys Inc, San Diego, Calif., U.S.A. (2005)).

Statistics:

The results were expressed as mean±standard deviation (SD). Comparison in each experiment was performed using an unpaired Student's t-test and a p value of less than 0.05 was considered to be statistically significant.

Experimental Results:

Chemical Identification of the Marine Terpenoids (Compounds 1 to 3):

The EtOAc extract of the freeze-dried specimen was fractionated by silica gel column chromatography and the eluted fractions were further separated utilizing normal phase HPLC to yield compounds 1 to 3. The novel compound 1 was named as 12,β-(3',β-hydroxybutanoyloxy)-20,24-dimethyl-24-oxo-scalara-16-en-25-al, and the novel compound 2 was named as 12β-(313-hydroxy-pentanoyloxy)-20,24-dimethyl-24-oxo-scalara-16-en-25-al. The known compound 3 was identified as 2-tetraprenil-1,4-benzochinone.

Figure 1:
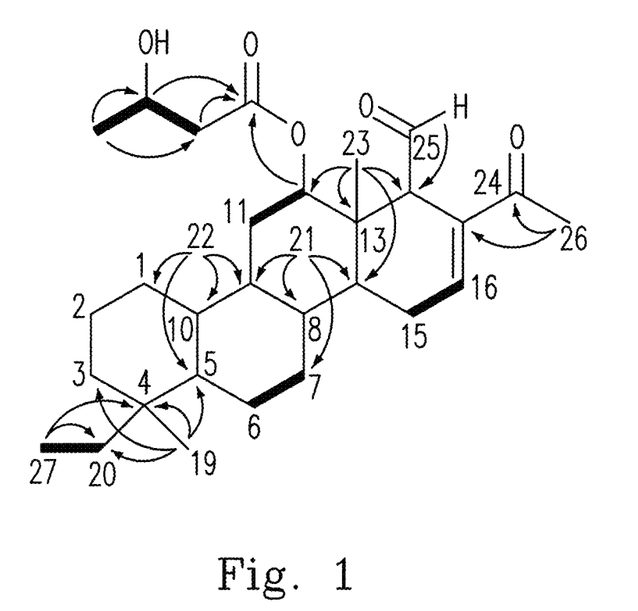
FIG. 1 is a diagram showing the $^1H$-$^1H$ COSY (-) HMBC (→) and NOESY (↔) correlations of compound 1 of the present invention.

Compound 1 was a colorless oil. The molecular formula of compound 1 was determined to be $C_{31}H_{48}O_6$ by HR-ESI-MS (m/z 523.3397 [M+Na]$^+$) and $^{13}C$ NMR data (Table 1), implying eight degrees of unsaturation. IR absorptions were observed at 3448, 1717 and 1665 cm$^{-1}$, suggesting the presence of hydroxyl, saturated carbonyl and α,β-unsaturated carbonyl functionalities. Resonances due to an aldehyde carbonyl carbon ($\delta_C$ 201.1), α,β-unsaturated carbonyl carbon ($\delta_C$ 198.2), ester carbonyl carbon ($\delta_C$ 172.1) and olefinic carbons ($\delta_C$ 142.9, CH; 138.4, C) in the $^{13}C$ NMR and distortionless enhancement by polarization transfer (DEPT) spectral data accounted for four double-bond equivalents, indicating a tetracyclic skeleton of compound 1. In the $^1H$ NMR data, resonances of one olefinic proton ($\delta_H$ 7.06, s) and two oxygenated methines ($\delta_H$ 4.86, dd, J=11.0, 4.5 Hz; 4.22, t, J=9.0 Hz) were observed. The planar structure and all of the $^1H$ and $^{13}C$ chemical shifts of compound 1 were elucidated by 2D NMR spectroscopic analysis, in particular $^1H$-$^1H$ correlation spectroscopy (COSY) and heteronuclear multiple bond correlation (HMBC) experiments (referring to FIG. 1), suggesting a characteristic scalarane-type sesterterpenoid structure. Compound 1 possess a 3-hydroxybutanoyloxy at C-12, a double bond at C-16/C-17, a ketone group at C-24 and an aldehyde group at C-25. The 3'R-configuration was determined by comparing the optical rotation (+10.7) of compound 1 with those of compound 2 (+5.7). Therefore, the structure of compound 1 possess the (4S*, 5S*, 8R*, 9R*, 10S*, 12R*, 13S*, 14S*, 18R*, 3'R*)-configuration.

TABLE 1

$^1H$ and $^{13}C$ NMR data of compounds 1 and 2
($^1H$: 500 MHz in CDCl$_3$; $^{13}C$: 125 MHz in CDCl$_3$.)

| | Compound 1 | | Compound 2 | |
|---|---|---|---|---|
| Position | $\delta_C$ | $\delta_H$ (J in Hz) | $\delta_C$ | $\delta_H$ (J in Hz) |
| 1 | 40.1, CH$_2$ | 0.88, 1.64 m | 40.1 | 0.87, 1.64 m |
| 2 | 18.1, CH$_2$ | 0.84 m | 18.1 | 0.84, 1.44 m |
| 3 | 36.5, CH$_2$ | 0.87 m; 1.66 br s | 36.5 | 0.87, 1.66 m |
| 4 | 36.1, C | | 36.1 | |
| 5 | 58.4, CH | 0.87 m | 58.4 | 0.88 m |
| 6 | 17.9, CH$_2$ | 0.85 m | 17.9 | 0.87 m |
| 7 | 41.9, CH$_2$ | 1.75 m | 42.0 | 1.74 m |
| 8 | 37.5, C | | 37.5 | |
| 9 | 58.0, CH | 0.99 m | 58.0 | 1.01 br s |
| 10 | 37.4, C | | 37.4 | |
| 11 | 23.3, CH$_2$ | 1.40 q (12.5); 1.87 dd (12.5, 4.0) | 23.2 | 1.88 m |
| 12 | 82.5, CH | 4.86 dd (11.0, 4.5) | 82.5 | 4.87 dd (11.0, 4.5) |
| 13 | 41.7, C | | 41.7 | |
| 14 | 53.0, CH | 1.21 m | 53.0 | 1.22 m |
| 15 | 23.6, CH$_2$ | 2.34 br t | 23.6 | 2.34 m |
| 16 | 142.9, CH | 7.06 s | 142.8 | 7.06 s |
| 17 | 138.4, C | | 138.5 | |
| 18 | 61.2, CH | 3.15 s | 61.2 | 3.17 s |
| 19 | 28.4, CH$_3$ | 0.80 s | 28.4 | 0.79 s |
| 20 | 24.4, CH$_2$ | 1.15 q (7.5); 1.52 m | 24.4 | 1.15, 1.50 m |
| 21 | 16.9, CH$_3$ | 0.96 s | 16.9 | 0.96 s |
| 22 | 17.3, CH$_3$ | 0.85 s | 17.3 | 0.85 s |
| 23 | 10.9, CH$_3$ | 0.98 s | 10.9 | 0.98 s |
| 24 | 198.2, C | | 198.2 | |
| 25 | 201.1, CH | 9.64 d (3.5) | 201.2 | 9.65 d (3.0) |
| 26 | 25.0, CH$_3$ | 2.28 s | 25.0 | 2.28 s |
| 27 | 8.6, CH$_3$ | 0.74 t (7.5) | 8.6 | 0.74 t (7.5) |
| 1' | 172.1, C | | 172.3 | |
| 2' | 43.4, CH$_2$ | 2.42 m | 41.6 | 1.14, 1.36 m |
| 3' | 64.3, CH | 4.22 t (9.0) | 69.4 | 3.96 t (11.0) |
| 4' | 22.5, CH$_3$ | 1.24 d (6.5) | 29.5 | 2.32 m |
| 5' | | | 9.9 | 0.96 t (4.0) |

The molecular formula of compound 2 was deduced as $C_{32}H_{50}O_5$ based on HR-ESI-MS (ion peak at m/z 537.3546 [M+$_{Na}$]$_+$ and $^{13}C$ NMR data suggesting that compound 2 possesses one more CM group compared with compound 1. The NMR data of compound 2 (Table 1) showed similarity to those of compound 1 with the replacement of one 3-hydroxybutanoyloxy group at C-12 in compound 1 by one 3-hydropentanolyoxy group in compound 2. The structure of compound 2 was further confirmed by the COSY correlations from H$_2$-29 to H$_3$-32 and by the HMBC correlations from H-12 and H$_2$-29 to C-28. Both compounds 1 and 2 were suggested to possess identical relative configuration based on the similarity in their NMR data. In order to identify the C-3' configuration on the 3-hydroxybutanoyloxy group, the (S)- and (R)-MTPA ester derivatives, 2s and 2r, were synthesized with (−)-(R)-MTPA-Cl and (+)-(S)-MTPA-Cl, respectively. The Δδ-values indicated 3'R-configuration (data not shown).

Apoptotic Induction of these Marine Terpenoids Via DNA Damage, MMP Dysfunction and Caspase Activation:

The antiproliferative effect of the two novel scalarane sesterterpenoids (compounds 1 and 2) and the compound 3 (as a tetraprenyltoluquinol-related metabolite) was evaluated using the MTT assay known by the skilled person in the art. Several cancer cell lines including leukemia K562, Molt 4, and HL 60 cells, prostate cancer LNCaP cells, colon cancer DLD-1 cells and breast cancer T-47D cells were used to evaluate the antiproliferative activity (referring to Table 2). Compound 1 exhibited the most potent cytotoxic activity with an IC$_{50}$ of 0.01 μg/mL (2.08 nM) against all leukemia and the lymphoma cell line U937. After a 72-hour treatment, the IC$_{50}$ values of compound 1 against DLD-1, T-47D, LNCaP, Ca9-22 and Cal-27 cells were 2.33, 2.19, 13.87, 0.1, and 0.56 μg/mL, respectively. The IC$_{50}$ values of compound 2 against leukemia K562, Molt 4 and HL 60 cells were 0.35 and 0.30, 0.22 μg/mL which were comparable to those of compound 3 (IC$_{50}$ values: 0.70, 0.34 and 0.42 μg/mL). Molt 4 cell line was the most sensitive cell line as demonstrated by the MTT assay known by the skilled person in the art. To detect whether the cytotoxic effect of these marine terpenoids was associated with the mitochondria-related apoptosis, the population of apoptosis and disruption of mitochondrial membrane potential in Molt 4 cells with annexin-V/PI and JC-1 staining were assessed. After 24 hours, compounds 1, 2 and 3 resulted in a dose-dependent (0, 0.0625, 0.125 and 0.25 μg/mL) increase in the apoptotic population of Molt 4 cells and disruption in mitochondrial membrane potential (data not shown). These results proved that the cytotoxic activity of these marine terpenoids are mediated through the mitochondrial dysfunction leading to the induction of apoptosis.

TABLE 2

Cytotoxic effects of compounds 1 to 3 against several cancer cell lines for 72 hours (IC$_{50}$, µg/mL)

| Compound | Leukemia | | | Lymphoma | | Oral | | Prostate | Colon | Breast |
|---|---|---|---|---|---|---|---|---|---|---|
| | K562 | Molt 4 | HL 60 | U937 | Sup-T1 | Ca9-22 | Cal-27 | LNCaP | DLD-1 | T-47D |
| 1 | 0.01 | 0.01 | 0.01 | 0.01 | 0.13 | 0.10 | 0.56 | 13.87 | 2.33 | 2.19 |
| 2 | 0.35 | 0.30 | 0.22 | 0.61 | 0.42 | 1.48 | 3.17 | NA[a] | 1.71 | 1.87 |
| 3 | 0.70 | 0.34 | 0.42 | 0.65 | 0.33 | 0.97 | 0.51 | NA[a] | 15.41 | 1.06 |
| Doxorubicin[b] | 0.20 | 0.01 | 0.02 | 0.21 | 0.02 | 0.05 | 0.01 | 2.47 | 1.28 | 0.08 |

[a]NA (non-active) = IC$_{50}$ >20 µg/mL for 72 hours.
[b]Positive control

Figure 2A:
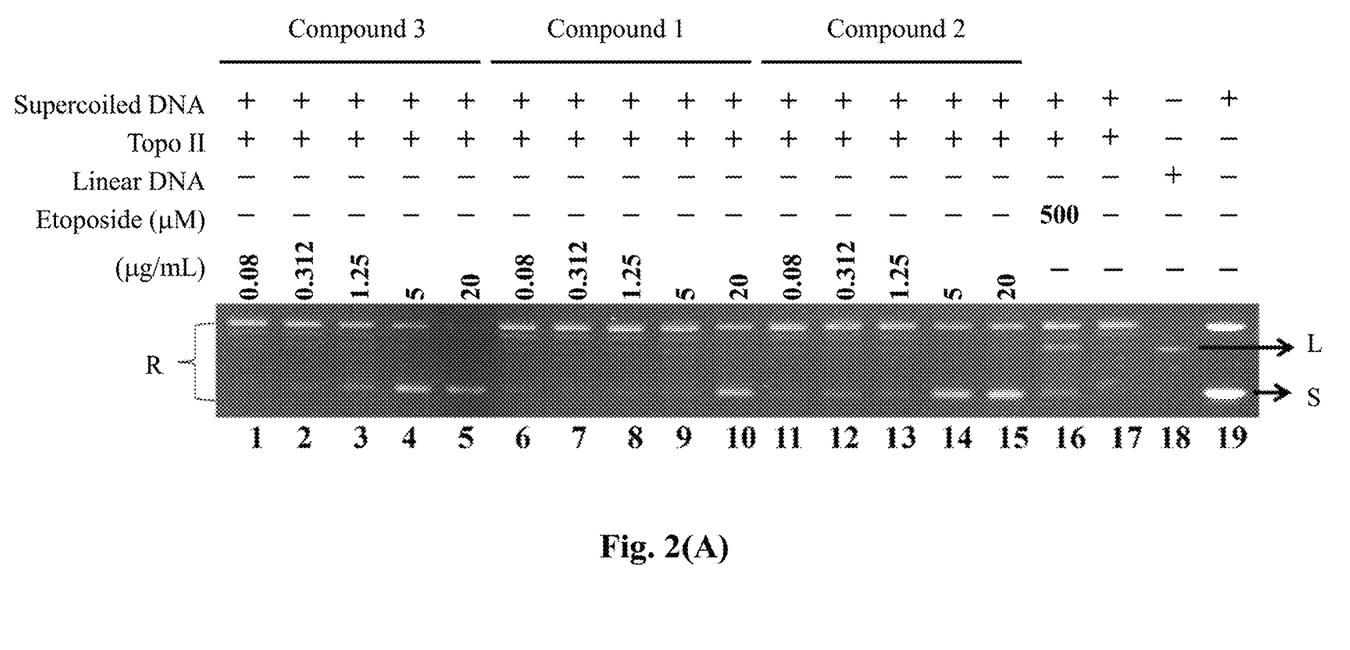
FIG. 2(A) is an electrophoretic gel diagram showing the effect of compounds 1 to 3 on the Topo II activity. Lanes 1-5: compound 3 (0.08, 0.3125, 1.25, 5, and 20 µg/mL); Lanes 6-10: compound 1 (0.08, 0.3125, 1.25, 5, and 20 µg/mL); Lanes 11-15: compound 2 (0.08, 0.3125, 1.25, 5, and 20 µg/mL); Lane 16: positive control, etoposide (500 µM), as a topo II poison (induction of linear DNA); Lane 17: plasmid DNA+topo II+solvent control (induction of DNA relaxation); Lane 18: Linear DNA; Lane 19: negative control plasmid DNA (supercoiled DNA).
Figure 2B:
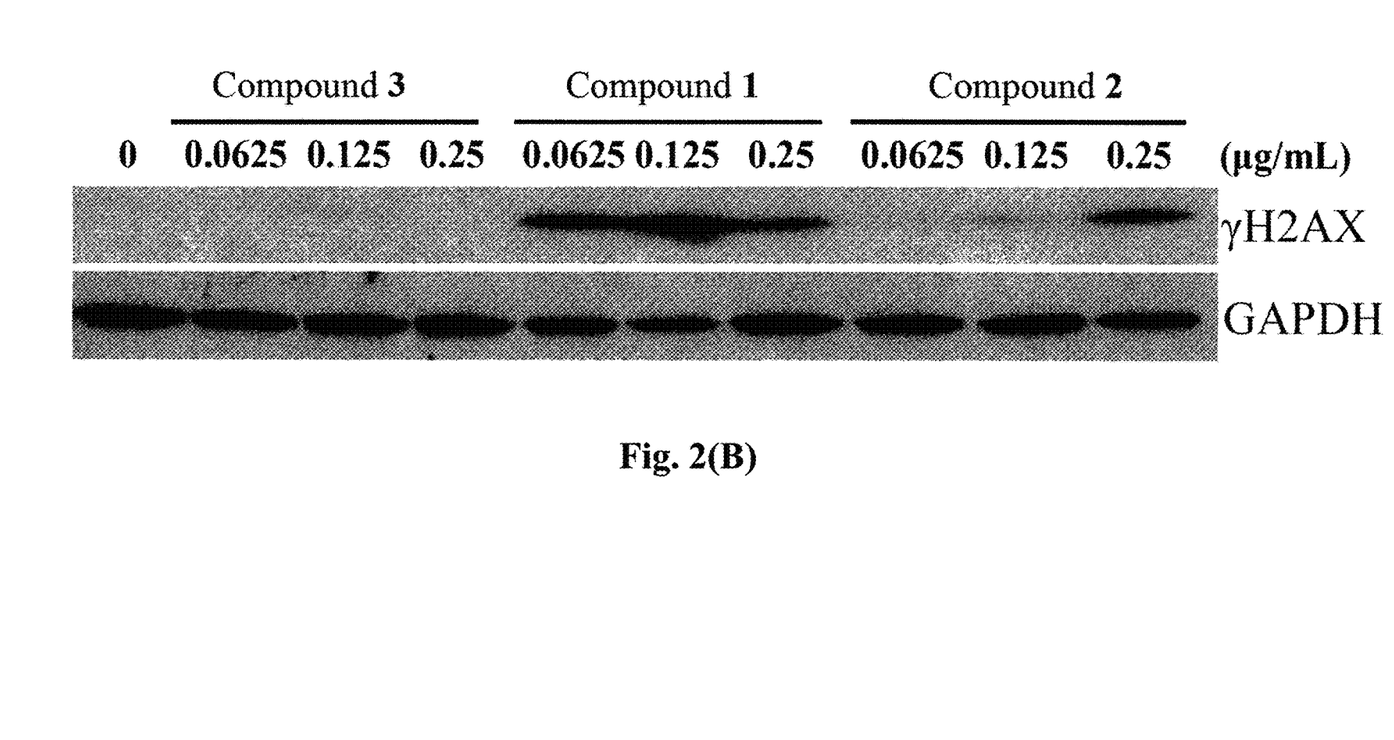
FIG. 2(B) shows the expression of γH2AX protein in Molt 4 cells induced by the treatment of the marine terpenoids (compounds 1 to 3) of the present invention. The cells were treated with compounds 1 to 3 (0, 0.0625, 0.125 and 0.25 µg/mL) for 24 hours, respectively. Protein expression was analyzed with Western blotting. GAPDH was used as the loading control.

In order to confirm whether the DNA damage-induced by the marine terpenoids of the present invention involved the inhibition of Topo II activity, a cell-free DNA cleavage assay using an enzyme-mediated negatively supercoiled pHOT1 plasmid DNA was applied. A linear DNA strand was observed upon treating the supercoiled pHOT1 plasmid DNA with etoposide, a standard topo II poison (FIG. 2(A), Lane 16, the control group). The use of compound 1 in increasing concentrations (0.08, 0.312, 1.25, 5, and 20 µg/mL) significantly inhibited DNA relaxation by 12, 13, 17, 20 and 99%, respectively, compared with the control supercoiled DNA and resulted in the formation of supercoiled DNA products in the presence of topo IIa (FIG. 2(A), Lanes 6-10). Additionally, compounds 2 and 3 significantly inhibited DNA relaxation by 12, 23, 36, 90 and 99% (FIG. 2(A), Lanes 11-15); and 7, 13, 28, 90 and 98% (FIG. 2(A), Lanes 1-5), respectively. These marine terpenoids suppressed Topo II activity, resulting in the inhibition of supercoiled DNA relaxation in a dose-dependent manner (FIG. 2(A)). Furthermore, compounds 1, 2 and 3 inhibited topo II activities with IC$_{50}$ of 1.98, 0.37 and 0.43 µg/mL, respectively as demonstrated by the cell-free system. To determine whether the apoptotic mechanism of compounds 1 to 3 affects γH2AX (as a biomarker of DNA damage) induction, Western blot analysis was employed to examine the activation of γH2AX. Compounds 1 and 2 significantly enhanced the expression of γH2AX in a dose-dependent manner, but the activation of DNA damage was not observed on compound 3 (FIG. 2(B)). These results suggested that these compounds 1 to 3 could act as potent catalytic inhibitors of Topo IIa.

Figure 3A:
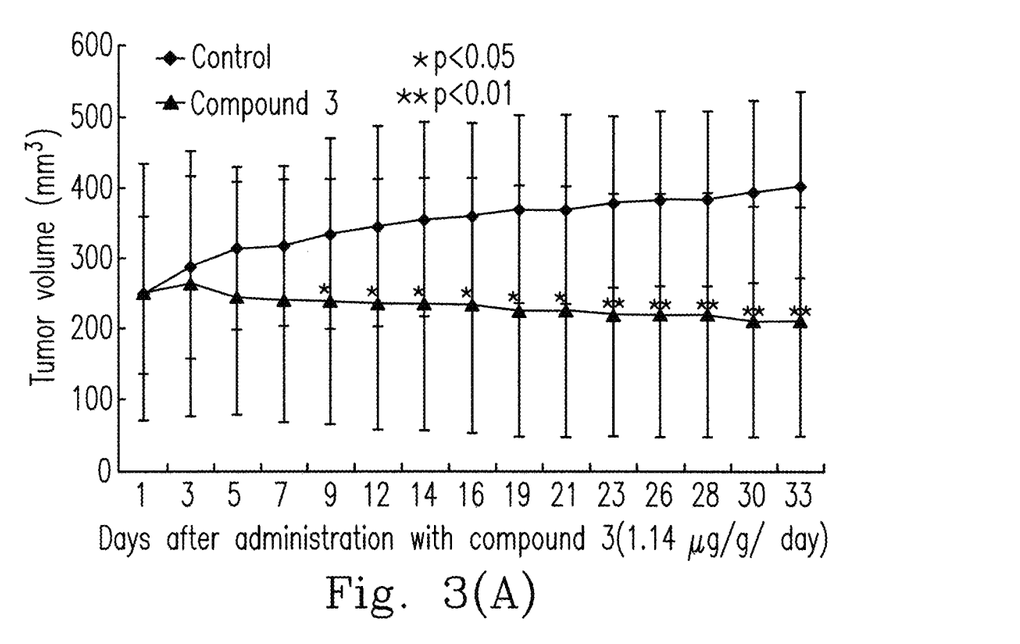
FIG. 3(A) is a diagram showing the effect of compound 3 on the tumor growth in an in vivo human Molt 4 tumor xenograft animal model. Tumor-bearing nude mice were intraperitoneally injected with solvent control (DMSO) and compound 3 (1.14 µg/g) for 33 days. Tumor volumes were measured every other day, and the results are expressed as mean±SD. *Significantly different from control groups at *p<0.05; **p<0.01. Control, n=8; compound 3, n=7.
Figure 3B:
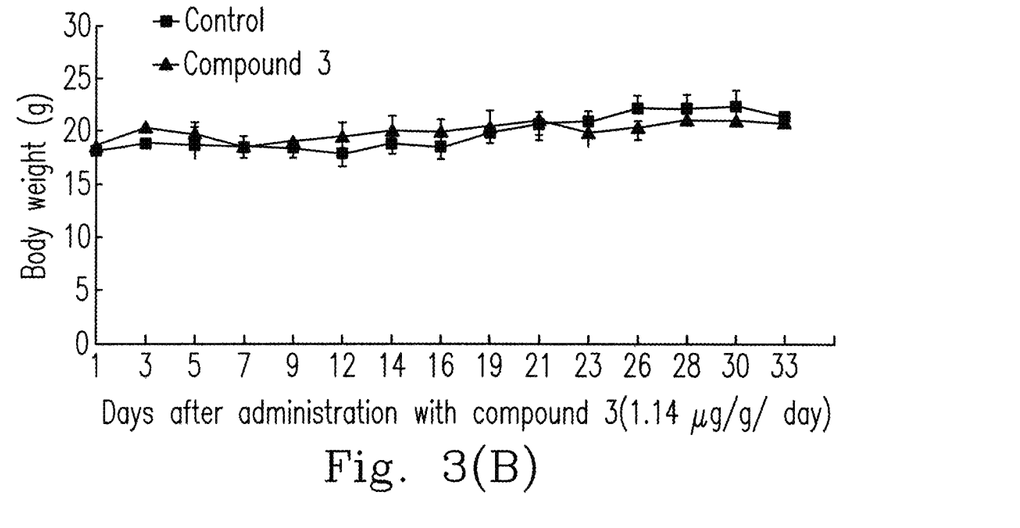
FIG. 3(B) is a diagram showing the effect of compound 3 on the body weight in the in vivo human Molt 4 tumor xenograft animal model. Tumor-bearing nude mice were intraperitoneally injected with solvent control (DMSO) and compound 3 (1.14 µg/g) for 33 days. The body weight were measured every other day, and the results are expressed as mean±SD. Control, n=8; compound 3, n=7.

Compound 3 Inhibited Tumor Growth in In Vivo Human Molt 4 Tumor Xenograft Animal Model:

Compounds 1 and 2 induced apoptosis in several cancer cell lines. On the other hand, compound 3 was used to study the in vivo anti-tumor activity by evaluating its effect on tumor growth of human leukemia Molt 4 in xenograft animal model. Molt 4 (1×10$^6$) cells were inoculated subcutaneously at the right flank of female immunodeficient athymic mice. After 33-day of treatment, the tumor growth of Molt 4 cells was significantly suppressed under the influence of compound 3 (1.14 µg/g) intraperitoneal injection. The average tumor size on day 33 in the control group was 404.63 mm$^3$, whereas the average tumor size in compound 3-treated group was 212.10 mm$^3$ (FIG. 3(A)). The tumor size was significantly lower in compound 3-treated group as compared to the control group (p<0.05) with no significant difference in the mice body weights (FIG. 3(B)). These results suggested that compound 3 exhibited anti-tumorigenic effect in vivo xenograft model.

Figure 4A:
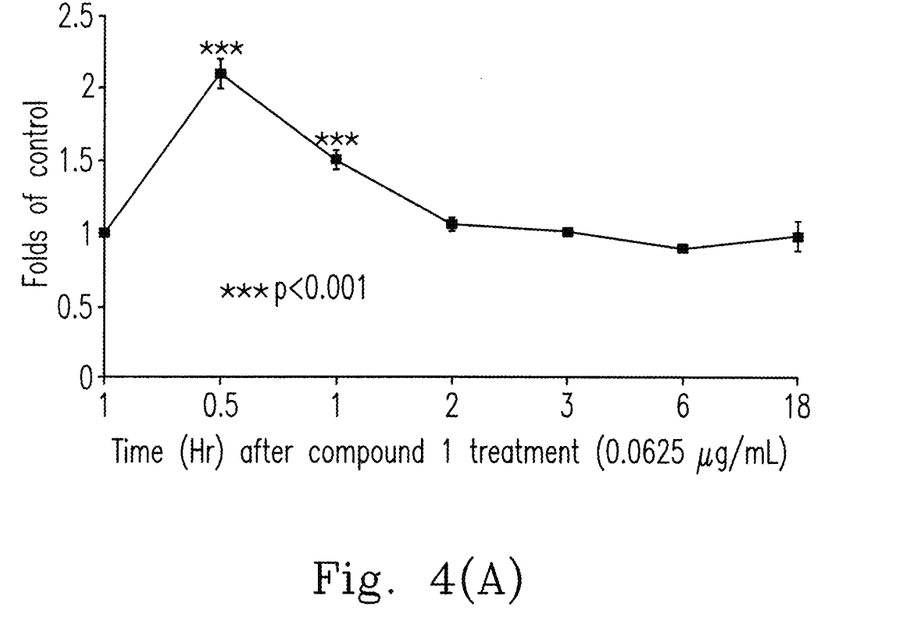
FIG. 4(A) is a diagram showing the effect of compound 1 on the ROS generation in Molt 4 cells.
Figure 4B:
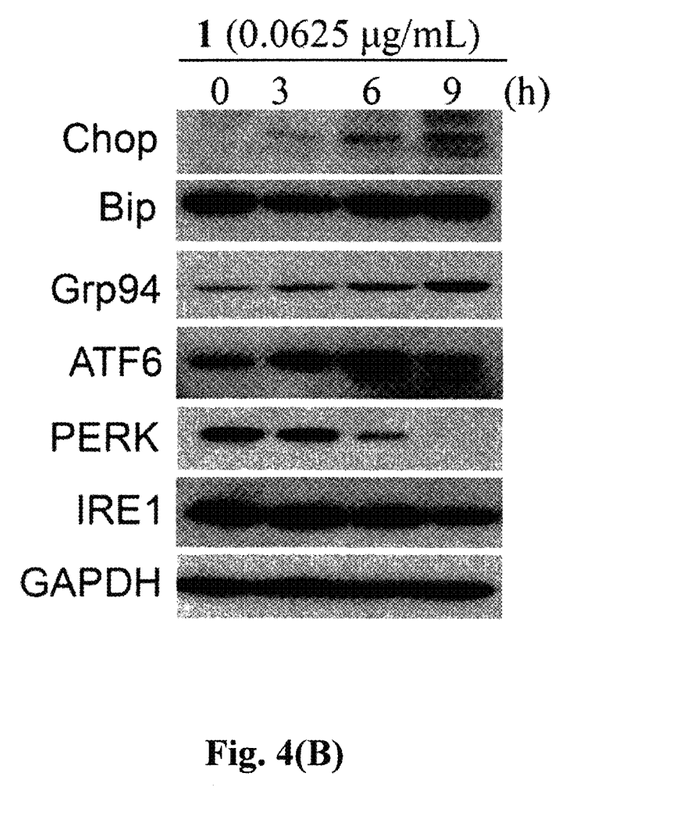
FIG. 4(B) is a diagram showing the effect of compound 1 on the ER-related protein in Molt 4 cells.
Figure 4C:
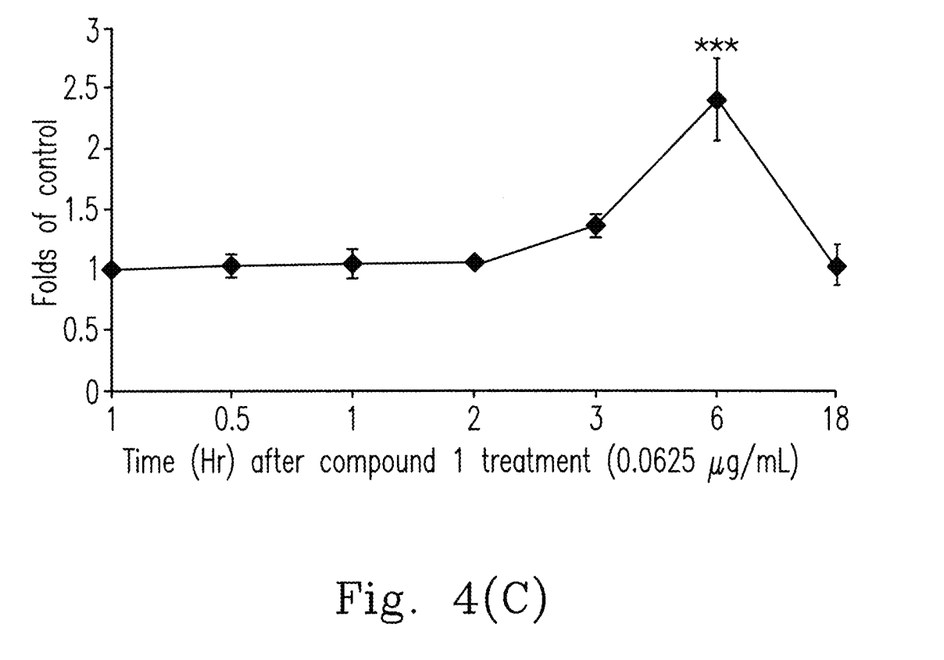
FIG. 4(C) is a diagram showing the effect of compound 1 on the calcium accumulation in Molt 4 cells.
Figure 4D:
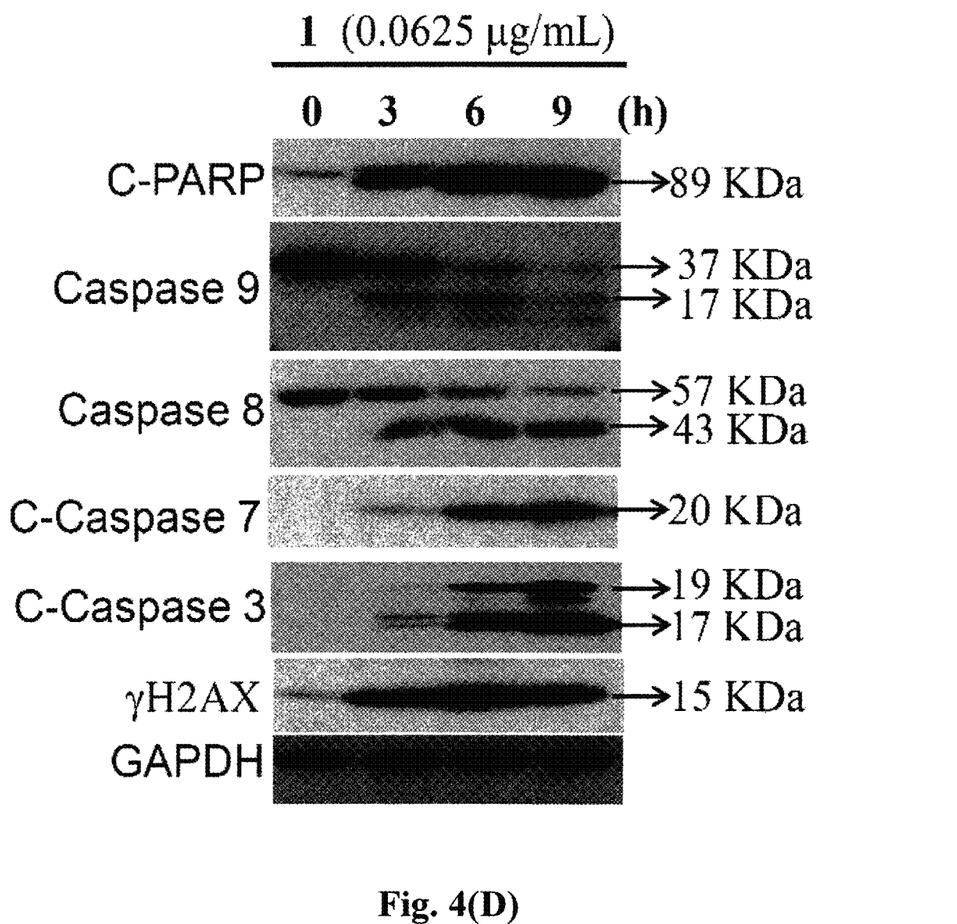
FIG. 4(D) is a diagram showing the effect of compound 1 on the apoptosis-related proteins in Molt 4 cells.
Figure 4E:
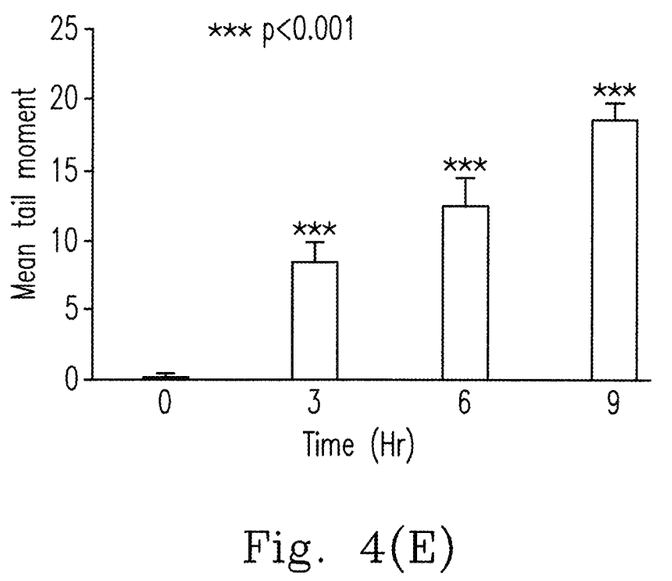
FIG. 4(E) is a diagram showing the effect of compound 1 on the "comet-tail" in Molt 4 cells.

Apoptotic Effect of Compound 1 Involves the Induction of ROS Generation, Endoplasmic Reticulum (ER) Stress and DNA Damage in Molt 4 Cells:

Oxidative stress is manifested by ROS overexpression and cannot be balanced by the available antioxidant machinery. Compound 1 of the present invention can damage the integrity of mitochondria, which are the major production sites of the superoxide anion, ozone. The induction of the intracellular formation of ROS by compound 1 was determined with a carboxyl derivative of fluorescein, carboxy-H2DCFDA dye using flow cytometric analysis. As shown in FIG. 4(A), treatment with compound 1 (0.0625 µg/mL) for 0.5, 1, 2 and 3 hours resulted in 2.09-, 1.51-, 1.06- and 1.01-fold increase in ROS levels, respectively, as compared with the mean fluorescence index (MFI) of the control. In addition, ROS generation could induce ER stress leading to mitochondria-related apoptosis. To further investigate if ER stress is involved in the apoptotic effect induced by compound 1, Western blot analysis was used to determine the expression of ER stress-related proteins. In a time-dependent manner, compound 1 promoted the levels of Bip, Chop, Grp 94 and the activation and cleavage of ATF 6 but suppressed the levels of PERK and IRE 1. Furthermore, the effect of compound 1 on the release of intracellular Ca$^{2+}$, was evaluated using fluorescent calcium indicator, Fluo 3. As shown in FIG. 4(C), the flow cytometric results showed that the treatment with compound 1 at different time intervals (0.5, 1, 2, 3, 6 and 18 hours) induced 1.03-, 1.05-, 1.06-, 1.37-, 2.41- and 1.06-folds increase in the intracellular Ca$^{2+}$ accumulation, respectively as compared to MFI of the control, indicating that ER stress was induced by compound 1 following the redox stress. Moreover, as shown in FIG. 4(D), PARP, caspases-8 and -9 cleavages were significantly increased in a time-dependent manner. In FIG. 4(D), the induction of the typical executor caspases-3 and -7, and γH2AX, was also observed using Western blot analysis. To confirm the induction of DNA damage by compound 1 in Molt 4 cells, a comet assay under neutral electrophoresis condition was utilized. Thus, the effect of compound 1 (0.0625 µg/mL) at different time intervals (0, 3, 6 and 9 hours) on the level of nuclear DNA integrity was determined. As shown in FIG. 4(E), compound 1 increased the degree of DNA migration in Molt 4 cells. The DNA migration was represented by the induction of DSBs in a time-dependent increase, as indicated by the abnormal tails' sizes in the comet assay.

Figure 5A:
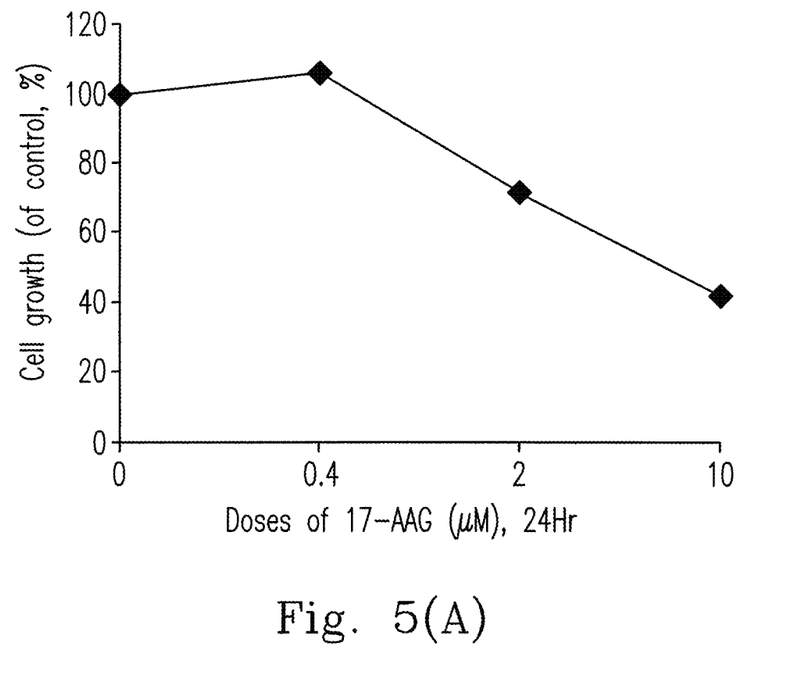
FIG. 5(A) is a diagram showing the cytotoxic effect of 17-AAG on Molt 4 cells.

Compound 1 as a Potent Inhibitor of Hsp90:

It is known that mitochondria are critical intracellular loci of ROS production and ROS exposure can lead to the 1-methyl-4-phenyl-1,2,3,6-tetrahydropyridine (mPTP) opening. The antioxidant, microsomal GST1, in the inner mitochondrial membrane can interact with the mitochondrial permeability transition (MPT) regulator proteins, such as ANT and/or CypD, to form a MPT pore contributing to mitochondria-mediated cell death. In addition, mitochondrial homeostasis of tumor cells is regulated by an organelle-specific Hsp90 chaperone network. To investigate whether the inhibition of Hsp90 participates in the apoptosis induced by compound 1, the molecular docking of Hsp90 with the available crystal structure was performed to gain insight of the compound 1 binding mode. Compound 1 could be docked to the N-terminal domain of Hsp90 with the binding energy of −10.93 Kcal/mol over the first Hsp90 N-terminal inhibitor, 17-AAG (−6.63 Kcal/mol), presumably because compound 1 formed non-classic hydrogen bonds with GLY132 and GLY135 at a distance of 3.27 Å and 3.66 Å; the classic hydrogen bonds with residues LYS112 (1.92 Å), PHE138 (2.31 Å and 2.45 Å) and ASN106 (2.45 Å); the hydrophobic bonds with residues ALA 55 (3.63 Å and 3.69 Å) and MET 98 (3.85 Å and 4.96 Å) (data not shown). According to the molecular docking experiments, compound 1 inhibits Hsp90 with an inhibition constant of 9.67 nM (>1430 folds) which was more potent than 17-AAG (10.83 μM). To fully understand the differences in activity between compound 1 and 17-AAG, the antiproliferative activity of 17-AAG in Molt 4 cells was examined by the MTT assay. As shown in FIG. 5(A), treatment of Molt 4 with increasing concentrations (0, 0.4, 2 and 10 μM of 17-AAG for 24 hours induced a suppression in cell growth with $IC_{50}$ values of 4.2 μg/mL (7.2 μM). According to the MTT results using Molt 4 cells, the antiproliferative activity of compound 1 (0.01 μg/mL, 19.1 nM) was 377 folds higher than that of 17-AAG.

Figure 5B:
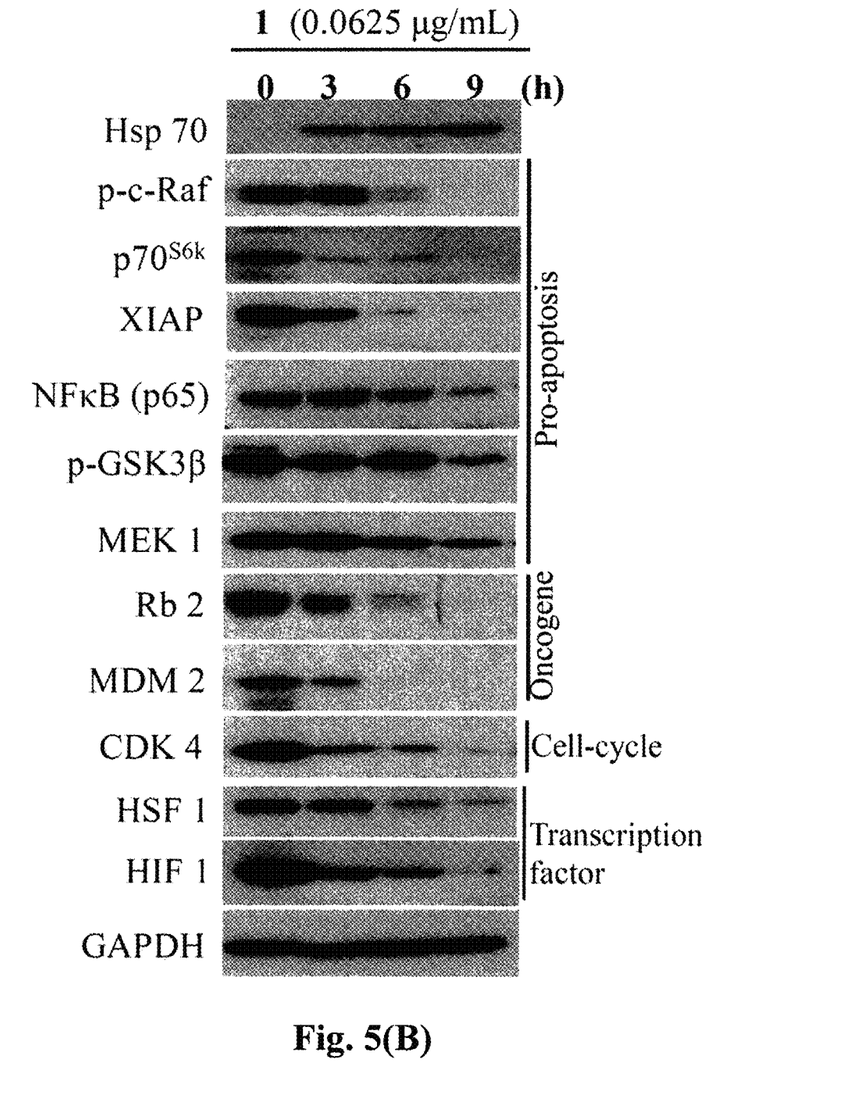
FIG. 5(B) is a diagram showing the effect of compound 1 on the expression of Hsp90 client proteins.

Hsp90 inhibitors induced the heat shock factor 1 (HSF 1)-dependent expression of Hsp70, and the genetic deletion of HSF 1 reduced the association of Hsp90 with its kinase client proteins. The induction of Hsp70 is the biomarker of Hsp90 with N-terminal inhibition. Aiming to understand the relation between Hsp90 function and the expression of Hsp70 and 90 clients, Molt 4 cells were treated with compound 1 (0.0625 μg/mL) for different time intervals. At first, the compound 1 treatment did not notably attenuate the expression of Hsp90 protein. The expression of Hsp70 increased in a time-dependent manner, as an established marker for the heat shock response (HSR) after Hsp90 inhibition, while surprisingly the expression of HSF 1 protein was attenuated with the compound 1 treatment in Molt 4 cells. Furthermore, as shown in FIG. 5(B), Hsp90 client proteins were suppressed, including $p70^{S6K}$, NFκB, Raf-1, p-GSK3β, MEK 1 and XIAP (pro-apoptotic protein), MDM 2 and Rb2 (oncoprotein), and CDK4 (cell cycle regulatory protein), HIF 1 and HSF1 (transcription factor). The majority of Hsps accumulate in subcellular localizations that determine whether a cell is going to die or differentiate. Furthermore, the localization of Hsp70 in response to the compound 1 treatment was identified using immunofluorescence by confocal microscope. In agreement with the Western blot results, the localization of Hsp70 was predominantly accumulated in cytosol and the accumulation increased with time (data not shown).

The Advantages of the Present Invention:

Two scalarane sesterterpenoids (compounds 1 and 2) and a known tetraprenyltoluquinol-related metabolite (compound 3) are isolated from the EtOAc extract of the sponge animal, *Carteriospongia* sp., in the present invention. All compounds 1 to 3 can be used in the anticancer, the reduction of the viability of cancer cells, and the inhibition of the Topo II catalytic activity. Compound 1 results in the abundant release of $Ca^{2+}$ and interferes the mitochondrial membrane potential, indicating that its apoptotic effect is mediated through the mitochondrial dysfunction. As demonstrated by the increase in the ROS generation, ATF6 cleavage and Chop expression, the compound 1-treatment firstly stimulates the ROS generation, perturbs the Bip/IRE1/PERK signal pathway and activates the Grp94/ATF6/Chop signal pathway implicated in ER stress, and the cytotoxic effect of compound 1 on the human leukemia Molt 4 cells is relevant to the induction of ER stress. Compound 1 possesses the potent Hsp90 and Topo II catalytic inhibitory activity as determined by the molecular docking and the cell-free system. The treatment of Molt 4 cells with compound 1 suppresses client protein expression and accumulation of Hsp70 in the cytosolic compartment as well as reduces the transcription factors (HSF 1 and HIF 1) expression.

Therefore, compounds 1 to 3 of the present invention can be used in anticancer, act as the topoisomerase II inhibitor, and can be prepared as anti-tumor pharmaceutical composition according to the pharmaceutical techniques and method.

While the invention has been described in terms of what is presently considered to be the most practical and preferred Embodiments, it is to be understood that the invention need not be limited to the disclosed Embodiments. On the contrary, it is intended to cover various modifications and similar arrangements included within the spirit and scope of the appended claims, which are to be accorded with the broadest interpretation so as to encompass all such modifications and similar structures.

What is claimed is:

1. A treatment method for treating a lymphoma of a subject, the method comprising: administering a pharmaceutically effective amount of a topoisomerase II inhibitor of formula (I) to the subject in need thereof:

formula (I)

where $R_1$ is one of —$CH_3$ and —$C_2H_5$.

2. The treatment method according to claim 1, wherein the topoisomerase II inhibitor of formula (I) is prepared by steps of:
   (a) providing a sponge animal;
   (b) extracting the sponge animal with ethyl acetate to obtain an ethyl acetate extract;
   (c) concentrating the ethyl acetate extract to obtain a residue; and
   (d) chromatographing the residue to obtain the topoisomerase II inhibitor of formula (I).

3. The treatment method according to claim 2, wherein the step (d) further comprises:
   (d1) sequentially chromatographing the residue with n-hexane, a plurality of n-hexane-ethyl acetate mixtures of an increasing polarity, and acetone on a silica gel to obtain a plurality of fractions; and
   (d2) purifying at least one of the plurality of fractions with a normal phase high performance liquid chromatography to obtain the topoisomerase II inhibitor of formula (I).

4. The treatment method according to claim 2, wherein the sponge animal is *Carteriospongia* sp.

5. The treatment method according to claim 2, wherein the topoisomerase II inhibitor of formula (I) with $R_1$ being —$CH_3$ acts as a heat shock protein 90 (hsp90) inhibitor.

* * * * *